(12) United States Patent
Silva et al.

(10) Patent No.: US 10,844,546 B2
(45) Date of Patent: *Nov. 24, 2020

(54) PROCESS FOR MANUFACTURING AN IMPROVED WEB MATERIAL BY THE IN-SITU MEASUREMENT AND ADJUSTMENT OF ION CONCENTRATION

(71) Applicants: Fernando Henrique-Pescatori Silva, Louveira (BR); Dale Kavalew, Cincinnati, OH (US)

(72) Inventors: Fernando Henrique-Pescatori Silva, Louveira (BR); Dale Kavalew, Cincinnati, OH (US)

(73) Assignee: Eldorado Brasil Celulose S.A., Sao Paulo (BR)

(*) Notice: Subject to any disclaimer, the term of this patent is extended or adjusted under 35 U.S.C. 154(b) by 83 days.

This patent is subject to a terminal disclaimer.

(21) Appl. No.: 16/207,131

(22) Filed: Dec. 1, 2018

(65) Prior Publication Data

US 2019/0315084 A1    Oct. 17, 2019

Related U.S. Application Data

(60) Provisional application No. 62/657,260, filed on Apr. 13, 2018.

(51) Int. Cl.
*D21H 23/78*    (2006.01)
*D21H 27/02*    (2006.01)
(Continued)

(52) U.S. Cl.
CPC ............. *D21H 23/78* (2013.01); *B31F 1/126* (2013.01); *D21F 5/181* (2013.01); *D21F 7/00* (2013.01);
(Continued)

(58) Field of Classification Search
CPC ...... D21H 17/66; D21H 21/14; D21H 21/146; D21H 23/12; D21H 23/50; D21H 23/52;
(Continued)

(56) References Cited

U.S. PATENT DOCUMENTS 5,096,539 A    3/1992 Allan
5,273,625 A    12/1993 Antolovich
(Continued)

FOREIGN PATENT DOCUMENTS

WO    02099185    12/2002
WO    2011017532    2/2011
(Continued)

OTHER PUBLICATIONS

L. H. Allen, Effects of System Closure on Retention and Drainage Aid Performance in TMP Newsprint Manufacture.
(Continued)

*Primary Examiner* — Jose A Fortuna
(74) *Attorney, Agent, or Firm* — Stephen T. Murphy Law LLC; Peter D. Meyer; Stephen T. Murphy

(57) ABSTRACT

A process having the steps of producing the web material with the papermaking machine; measuring a molar amount of a monovalent inorganic ionizable cation species (MIICS) in the web material; measuring a molar amount of a divalent inorganic ionizable cation species (DIICS) in the web material; calculating a molar ratio of the measured molar amount of the MIICS to the measured molar amount of the DIICS in the web material; determining if the molar ratio of MIICS to DIICS is about less than or equal to 10; and, if the molar ratio of MIICS to DIICS is greater than about 10, adding an amount of DIICS to the papermaking machine to adjust the molar ratio of MIICS to DIICS so the web material adhering
(Continued)

to the Yankee drum drying system has a molar ratio of MIICS to DIICS of about less than or equal to 10, is disclosed.

34 Claims, 2 Drawing Sheets

(51) Int. Cl.
```
D21H 21/14      (2006.01)
D21H 23/56      (2006.01)
G01N 33/34      (2006.01)
B31F 1/12       (2006.01)
D21H 23/12      (2006.01)
D21F 11/00      (2006.01)
D21F 11/14      (2006.01)
D21H 23/50      (2006.01)
D21H 23/52      (2006.01)
D21F 7/00       (2006.01)
D21F 5/18       (2006.01)
D21G 9/00       (2006.01)
B31F 1/14       (2006.01)
```

(52) U.S. Cl.
CPC .......... *D21F 11/006* (2013.01); *D21F 11/145* (2013.01); *D21G 9/0018* (2013.01); *D21H 21/146* (2013.01); *D21H 23/12* (2013.01); *D21H 23/50* (2013.01); *D21H 23/52* (2013.01); *D21H 23/56* (2013.01); *D21H 27/02* (2013.01); *G01N 33/34* (2013.01); *B31F 1/14* (2013.01)

(58) Field of Classification Search
CPC ...... D21H 23/56; D21H 23/78; D21H 25/005; D21H 27/02; D21F 11/006; D21F 11/145; D21F 5/181; D21F 7/00; B31F 1/126; B31F 1/14; D21G 9/0018; D21G 9/0036; G01N 33/34; G01N 33/346
See application file for complete search history.

(56) References Cited

U.S. PATENT DOCUMENTS

```
7,744,722   B1   6/2010   Tucker
2019/0315084 A1* 10/2019  Silva ................... D21H 25/005
2019/0316297 A1* 10/2019  Silva ....................... D21F 5/181
```

FOREIGN PATENT DOCUMENTS

```
WO      2012012316         1/2012
WO      2016190801         12/2016
WO      WO-2019197862 A1 * 10/2019  ............. D21H 21/14
```

OTHER PUBLICATIONS

A. Blanco, C. Negro, and J. Tijero, Influence of Salt on the Interation of Polymers With the Different Pulp Fractions, Papermakers Conference, 1994.

Jonna Boudreau and Ulf Germgard, Influence of Various Pulp Properties on the Adhesion Between Tissue Paper and Yankee Cylinder Surface, Bioresources.com, 2014.

P.H. Brouwer, Consequences of the Zero Soluble and Surface Charge Wet-End Approach for Other Papermaking Operations Like Surface Sizing, Coating, Pitch Control, Etc., Papermakers Conference, 1992.

Arthur Charles Dreshfield, Jr., A Study of Transverse Moisture Distribution and Movement During Hot-Surface Drying of Paper, Jun. 1956.

A. A. Elisabeth Horvath, Appropriate Conditions for Polyelectrolyte Titration to Determine the Charge of Cellulosic Fibers, Stockholm, 2003.

Martin A. Hubbe, syed Hadi Hasan, and Joel J. Ducoste, Cellulosic Substrates for Removal of Pollutants From Aqueous Systems: A Review. 1.Metals, bioresources.com, 2011.

Jennie Jansson, The Influence of PH on Fiber and Paper Properties, Karlstad University, Jun. 17, 2015.

Hanna Lindquist, Improvement of Wet and Dry Web Properties in Papermaking by Controlling Water and Fiber Quality, Abo Akademi University, Finland, 2013.

Paulina Mocchiutti and Miguel Zanuttini, A Useful Equation for Estimating the Surface Charge of Pulp Fibers, Tappi Journal, May 2005.

A.M.A. Nada, W.M. Moussa, Abd El-Mongy and E.S. Abd El-Sayed, Physicochemical Studies of Cation Ion Exchange Wood Pulp, Australian Journal of Basic and Applied Sciences, 2009.

Donald A. Pietschker, The 100% Closed Water System—What to Expect, Papermakers Conference, 1996.

Alan W. Rudie, Alan Ball, Narendra Patel, Ion Exchange of H+, Na+, Mg2+, Ca2+, Mn2+, and Ba2+ on Wood Pulp, Journal of Wood Chemistry and technology, 26: 259-272, 2006.

Per Stenius, Surface Chemistry and Charge of Cellulosic Fibres, Aalto University, Helsinki/Expoo, Finland (no date).

W. Yantasee and G.L. Rorrer, Comparison of Ion Exchange and Donnan Equilibrium Models for the PH-Dependent Adsorption of Sodium and Calcium Ions Onto Kraft Wood Pulp Fibers, Journal of Wood Chemistry and Technology, Feb. 16, 2007.

Jim Zhang, Robert Pelton, Lars Wagberg, and Mats Rundlof, The Effect of Molecular Weight on the Performance of Paper Strength Enhancing Polymers, Journal of Pulp and Paper Science, May 2001.

* cited by examiner

PROCESS FOR MANUFACTURING AN IMPROVED WEB MATERIAL BY THE IN-SITU MEASUREMENT AND ADJUSTMENT OF ION CONCENTRATION

FIELD OF THE INVENTION

The present invention relates to the production of tissue and towel paper web structures that incorporate the use of a Yankee dryer. These processes relate to the specific ionic characteristics present in the fibrous materials used to make these web structures and adjusting the molar ratio of certain ions present in the fibrous materials that make the Yankee creping adhesive more stable and controllable. This stabilization is achieved by adjusting the molar ratios of divalent and monovalent ions at various locations in the pulp making and papermaking processes.

BACKGROUND OF THE INVENTION

Web materials having enhanced softness, absorbency, and strength (temporary and permanent), such as tissue and towel products, are desired by consumers. To this end, work continues and attempts to find new ways produce these web materials to better meet this consumer desire. "Web material(s)", "fibrous web(s)", and "fibrous structure(s)" are all intended to be utilized interchangeably throughout this document to reference structures that result in, or are useful for, tissue and/or towel products.

"Softness" is the tactile sensation that is the result of a user's perception based on the web material drape over their hand, the way the surface of the web material feels against their fingers and/or how the implement feels as it is folded or crumpled in their hand. This tactile sensation is a result of a combination of several physical properties of the paper sheet including the bulk, strength, and stretchability of the paper.

"Creping" is a process that mechanically foreshortens a fibrous structure in the machine and/or cross-machine directions to enhance the softness, bulk and stretchability of the final web material. Foreshortening refers to the reduction in length of a dry (having a consistency of at least about 90% and/or at least about 95%) fibrous web which occurs when energy is applied to the dry fibrous web in such a way that the length of the fibrous web is reduced and the fibers in the fibrous web are rearranged with an accompanying disruption of fiber-fiber bonds.

A creped web substrate can be formed with a flexible blade (a "creping blade") placed against a heated drying cylinder such as a Yankee dryer (also called a "Yankee drum drying system" herein). A partially dry fibrous structure is adhered to the surface of a Yankee dryer and then rotates with the surface of the Yankee dryer until contact with the creping blade removes it from the surface of the Yankee dryer. The degree to which the fibrous structure is adhered to the surface of the Yankee dryer prior to creping can be considered a key factor to determine the degree of softness, bulk, and stretchability exhibited by the fibrous structure after creping.

It is understood that the paper machine (also referred to as a papermaking machine throughout) operating conditions and specific unit operations of a paper machine can have a great impact on Yankee creping adhesive appearance and performance. Furthermore, the interface between the Yankee dryer surface and the web material is a thin film comprising an agglomeration of materials that results from both materials directly added to the process via the Yankee dryer creping adhesive, but also materials that are carried to the Yankee dryer via the web material, the fibers contained in the web material, and the specific operating system and equipment used in making these web materials. The Yankee creping adhesive is therefore both constructed of and influenced by the pulps used to make the structure, inorganic contaminants and chemicals sold to manage and control these materials.

Since the creping process has an impact on the softness, bulk, and stretchability of the resulting final product intended for the web material, the creping process is considered a key transformation step commonly used in the manufacture of tissue, facial and towel grades of paper. Without desiring to be bound by theory, it is believed that creping creates micro and macro folds in the web material that can increase the bulk, softness and absorbency of the web material.

To facilitate a good crepe quality, many papermakers add a creping adhesive formulation to the Yankee dryer prior to contact with the partially dry fibrous structure to enable good adhesion. The creping adhesive formulation may comprise one or more adhesive components such as water-soluble adhesive polymers, one or more release agent components, and/or other desired additives that may achieve the desired partially dry fibrous structure/Yankee dryer contact and impart desired properties to the resulting web material. The chemical mixture applied to the surface of the Yankee dryer prior to adhesion of the partially dry fibrous structure is commonly referred to as a "creping adhesive".

The level of adhesion of the partially dry fibrous structure to the Yankee dryer surface is also of importance as it influences the ability and capability of a partially dry fibrous structure to dry during its short time in contact with the Yankee dryer. Higher levels of adhesion permit better heat transfer but can also affect the ability of a dried partially dry fibrous structure to be released from the Yankee dryer surface, and therefore creped. Increased drying capability is desired, as improving the drying capability may allow the machine to operate at higher speeds.

Historically, before the development of the creping adhesive, adhesion of the partially dry fibrous structure to the Yankee dryer surface was accomplished through the presence of naturally occurring hemicellulose present in the individual pulp fibers. Hemicellulose deposits have been observed forming on the Yankee dryer surface can vary and, at times the tackiness of the hemicellulose changes to cause these deposits to contain fiber fragments picked out of the fibrous structure, resulting in a heavy film, holes in the sheet, sheet breaks, and poor crepe quality.

Another problem associated with the use of the creping adhesive is an excessive build-up of the creping adhesive on the Yankee dryer surface. While some amount of buildup of the creping adhesive on the Yankee dryer is essential to protect the dryer shell, excessive buildup can produce streaks, which impact the profile of adhesion across the width of the Yankee dryer surface. This buildup can result in sheet bumps, wrinkles, wet spots and sheet breaks in the finished web material. A second blade, known as a cleaning blade can scrape the Yankee dryer surface to remove excess creping adhesive and any other residue left behind on the Yankee dryer surface. This requires extra process steps to change both the creping and the cleaning blades frequently to prevent excessive buildup of adhesive coating and ensure good crepe quality.

One of skill in the art can use polyamidoamine-epichlorohydrin resins (PAE resins) as creping adhesives. PAE resins can incorporate hypophosphorous acid and its salts as an antioxidant and/or a stabilizer in polymeric formulations, polyamides, and alkyd resins. Polymers stabilized by hypophosphorous acid and its salts are all water-insoluble materials.

While the Yankee creping adhesive choices are adapted to create a more reliable Yankee creping adhesive to solve crepe quality concerns, tissue sheet creping reliability improvement continues to be a focus area of increasing importance.

Additionally, the reduction of water consumption in pulp and papermaking operations is a global goal that has been a long-term focus for cost reduction reasons. However, water consumption reduction is also critical to attain new sustainability/environmental goals. Those skilled in the art recognize that reduction of water consumption involves the increased closure of a papermaking water circuit. Closure of the papermaking process water circuit generally results in the build-up of non-process elements, most of which are cationic and anionic in nature. The build-up of fines may also take place, but these are anionic in nature. The buildup of cationic compounds leads to poor paper formation and adversely affects the production throughput and paper machine runnability, due to sheet breaks and their resulting production losses when they exceed the isoelectric point.

Closure of the papermaking water system can result in higher suspended solids, higher dissolved solids, increased temperature and reduced dissolved oxygen. This can lead to increased corrosion, increased deposition, increased microbiological activity, reduction in additive efficiency and reduction in finished product quality.

Those skilled in the art recognize that papermaking operations require a stable and slightly anionic environment to allow proper fiber-to-fiber bonding and web material sheet formation. Wood pulp fibers used to make the web materials discussed herein are generally anionic in nature due to certain residual functional groups, namely carboxylic acid and phenolic hydroxyl carried over with the non-extracted hemicellulose and lignin fragments. Carboxylic acids are weakly dissociated and the carboxylate moiety (—COO$^-$) present on wood pulp fibers acts as an anionic site for cation exchange at the proportion of one mole of functional group on the pulp. As the pH increases, carboxylic acid groups in wood pulp dissociate until the amount of alkali added is the same as the amount of existing charged groups. The carboxylate acts as a weak-acid cation exchanger that is not highly dissociated and will not readily exchange H$^+$ ions as strong creping adhesives (resins) do. In other words, wood pulp fibers exhibit a weak-acid resin (WAR) character.

WAR exchangers require the presence of some alkaline species to react with the more tightly bond hydrogen ions of the creping adhesive as in the reaction:

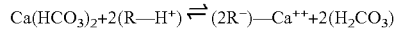

$$Ca(HCO_3)_2 + 2(R\text{—}H^+) \rightleftharpoons (2R^-)\text{—}Ca^{++} + 2(H_2CO_3)$$

Those skilled in the art recognize that it is common in a tissue/towel papermaking operation to add alkaline agents to the pulper or white water complex for pH control, better slushing of the pulp bales, and improved fiber swelling. Those skilled in the art will also recognize that it is common in tissue and towel papermaking operations to add acidic agents to the pulper or white water complex for pH control. The choice of whether a papermaker adds acid or alkaline agents depends upon the papermaking strength additives, water supply source and quality and/or other papermaking or product considerations. The exchange process is a neutralization reaction with the alkaline HCO$_3^-$ neutralizing the H$^+$ of the resin. WAR, such as wood pulp or cellulose, will split alkaline salts (NaHCO$_3$) but not non-alkaline salts (NaCl or Na$_2$SO$_4$). Weak-acid cation ion exchange resins are used to remove the cations associated with high alkalinity, such as the counter-ions of CO$_3^{-2}$, OFF and HCO$_3^-$, and low in dissolved CO$_2$ and sodium.

In making wood pulp for a papermaking operation, during the unit operations of digesting and bleaching, the anionic sites are electrically compensated by a counter-ion that is cationic in nature. This can include typically sodium, calcium and/or magnesium, among others in minor amounts. Different pulps may have a larger or smaller amount of anionic sites present that are fully or partially neutralized even in the presence of excess counter-ions, which are not bond to pulp but present as residual ash. The amount of bonding ions available can depend on the wood raw material, the pulping, bleaching and washing operational conditions.

Those skilled in the art recognizes that pulp beating (i.e., refining) can increase the accessible surface charge groups, allowing easier access to such groups in the fibers. Those of skill in the art will readily recognize that pulp beating and other pulp handling techniques (i.e., refining) can increase the accessible surface charge groups, allowing easier access to such groups in the fibers, while the total isoelectric charge changes with beating or refining. The amount of metal ions in the pulp is, however, in the same order as the amount of acid groups.

The processes used for the manufacture of certain pulp fibers can result in saleable pulps that lack divalent ions commonly observed in past pulp fibers. When these pulps are dried, they show a significant ash reduction versus their peers. Further, these pulps also show a much higher molar ratio of monovalent ions bound to the carboxyl groups compared to divalent ions. This is problematic as local pulp mills incorporate closed water systems and/or are located or re-located to parts of the world where soft water is used in the pulp making process.

It has also been observed that fibrous pulps having a higher percentage of monovalent ions attached to the surface may result in significant runnability problems in tissue and towel processes due to Yankee dryer/creping adhesive adhesion issues. It is also believed that these fibers have a lower chemical efficiency than competitive pulp fibers.

Further, while not being bound to any particular theory, it is believed that the "Dreshfield effect" can be linked to the rationale as to why pulp mills with a higher degree of closed water systems and/or papermaking operations with substantially closed water systems have Yankee creping adhesive-related issues. By way of example, the Yankee drying process in tissue and towel machines happens quite fast (in seconds) with a starting dryness of around 30-60% and ending in a dryness in excess of 90%. During this drying process, the ions present in the partially dry fibrous structure (i.e., web material) migrate via the Dreshfield effect. Not be bound to theory, the Dreshfield effect provides that water migrates from the core of a partially dry fibrous structure to the outer part of the partially dry fibrous structure carrying soluble and colloidal materials. These soluble and colloidal materials then concentrate at the outer layers of the partially dry fibrous structure. As one of the sides of the partially dry fibrous structure is adhered to the surface of the Yankee dryer, the soluble and colloidal materials disposed on the adhered surface of the partially dry fibrous structure can quickly react with the creping adhesive disposed upon the surface of the Yankee dryer. It is believed that specific ion types present in the soluble and colloidal materials disposed upon the surface of the partially dry fibrous structure deleteriously react with the Yankee creping adhesive. This results in a web material having defects present therein being removed (i.e., creped") from the surface of the Yankee dryer. It was surprisingly discovered that having the correct ion types present within the partially dry fibrous structure would clearly mitigate these ineffective interactions and likely result in a better quality web material being creped off the surface of the Yankee dryer.

Thus, it would be a clear advantage for tissue and towel manufacturing systems to provide a method that addresses the impact of the changing ionic nature of the incoming fiber sheet (i.e., web material) on Yankee creping adhesive. It would also be a clear advantage to provide a process that mitigates this impact via an ion exchange process whereby specific inorganic ions in defined specific molar ratios can be used to mitigate the observed deleterious Yankee creping issues and thereby create a more robust system via ion exchange of the web material. It would also be advantageous to provide a method of producing creped tissue and towel paper products that exhibit improved process capability, improved Yankee dryer reliability, improved drying efficiency, and improved tissue/towel product crepe quality. Further, it would be an advantage to provide a tissue making process that is more capable of mitigating process upsets that may result from changes in pulp supply and/or pulp suppliers because the pulp raw material supply used to produce these tissue and towel products having different levels of cationic salt or mono/divalent metal ions due to the use of closed loop water systems or pulp supplies that are naturally deficient in hardness and/or divalent cations.

SUMMARY OF THE INVENTION

The present disclosure provides a process for manufacturing a web material on a papermaking machine having a Yankee drum drying system. The process comprises the steps of: a) producing the web material with the papermaking machine; b) measuring a molar amount of a monovalent inorganic ionizable cation species (MIICS) in the web material; c) measuring a molar amount of a divalent inorganic ionizable cation species (DIICS) in the web material; d) calculating a molar ratio of the measured molar amount of the MIICS to the measured molar amount of the DIICS in the web material; e) determining if the molar ratio of MIICS to DIICS is about less than or equal to 10; and, f) if the molar ratio of MIICS to DIICS is greater than about 10, adding an amount of DIICS to the papermaking machine to adjust the molar ratio of MIICS to DIICS so the web material adhering to the Yankee drum drying system has a molar ratio of MIICS to DIICS of about less than or equal to 10.

The present disclosure also provides a process for manufacturing a web material on a papermaking machine having a Yankee drum drying system. The process comprises the steps of: a) producing the web material with the papermaking machine; b) measuring a molar amount of a monovalent inorganic ionizable cation species (MIICS) in the web material; c) measuring a molar amount of a divalent inorganic ionizable cation species (DIICS) in the web material; d) calculating a molar ratio of the measured molar amount of the MIICS to the measured molar amount of the DIICS in the web material; e) determining if the molar ratio of MIICS to DIICS is about less than or equal to 10; and, f) if the molar ratio of MIICS to DIICS is greater than about 10, applying an amount of DIICS to a surface of the Yankee drum drying system to adjust the molar ratio of MIICS to DIICS so the web material adhering to the Yankee drum drying system has a molar ratio of MIICS to DIICS of about less than or equal to 10.

The present disclosure further provides a process for manufacturing a web material on a papermaking machine having a Yankee drum drying system. The process comprises the steps of: a) producing the web material with the papermaking machine; b) measuring a molar amount of a monovalent inorganic ionizable cation species (MIICS) in the web material; c) measuring a molar amount of a divalent inorganic ionizable cation species (DIICS) in the web material; d) calculating a molar ratio of the measured molar amount of the MIICS to the measured molar amount of the DIICS in the web material; e) determining if the molar ratio of MIICS to DIICS is about less than or equal to 10; and, f) if the molar ratio of MIICS to DIICS is greater than about 10, applying an amount of DIICS to the web material after the web material has been adhered to a surface of the Yankee drum drying system to adjust the molar ratio of MIICS to DIICS so the web material adhered to the Yankee drum drying system has a molar ratio of MIICS to DIICS of about less than or equal to 10.

The present disclosure yet further provides a process for manufacturing a web material on a papermaking machine having a Yankee drum drying system. The process comprises the steps of: a) providing the papermaking machine with a white water loop section, the white water loop section providing the papermaking machine with an aqueous stream; b) producing the web material with the papermaking machine; c) measuring a molar amount of a monovalent inorganic ionizable cation species (MIICS) in the web material; d) measuring a molar amount of a divalent inorganic ionizable cation species (DIICS) in the web material; e) calculating a molar ratio of the measured molar amount of the MIICS to the measured molar amount of the DIICS in the web material; f) determining if the molar ratio of MIICS to DIICS is about less than or equal to 10; and, g) if the molar ratio of MIICS to DIICS is greater than about 10, adding an amount of DIICS to the white water loop section of the papermaking machine to adjust the molar ratio of MIICS to DIICS in the aqueous stream to about less than or equal to 50.

The present disclosure still further provides a process for manufacturing a web material on a papermaking machine having a Yankee drum drying system. The process comprises the steps of: a) providing the papermaking machine with a fresh water makeup system, the fresh water makeup system providing the papermaking machine with an aqueous stream; b) producing the web material with the papermaking machine; c) measuring a molar amount of a monovalent inorganic ionizable cation species (MIICS) in the web material; d) measuring a molar amount of a divalent inorganic ionizable cation species (DIICS) in the web material; e) calculating a molar ratio of the measured molar amount of the MIICS to the measured molar amount of the DIICS in the web material; f) determining if the molar ratio of MIICS to DIICS is about less than or equal to 10; and, g) if the molar ratio of MIICS to DIICS is greater than about 10, adding an amount of DIICS to the fresh water makeup system of the papermaking machine to adjust the molar ratio of MIICS to DIICS in the aqueous stream is about less than or equal to 50.

The present disclosure still yet further provides a process for manufacturing a web material on a papermaking machine having a Yankee drum drying system. The process comprises the steps of: a) supplying the Yankee drum drying system with a creping adhesive; b) applying the creping adhesive to a surface of the Yankee drum drying system; c) producing the web material with the papermaking machine; d) measuring a molar amount of a monovalent inorganic ionizable cation species (MIICS) in the web material; e) measuring a molar amount of a divalent inorganic ionizable cation species (DIICS) in the web material; f) calculating a molar ratio of the measured molar amount of the MIICS to the measured molar amount of the DIICS in the web material; g) determining if the molar ratio of MIICS to DIICS is about less than or equal to 10; and, h) if the molar ratio of MIICS to DIICS is greater than about 10, adding an amount of DIICS to the creping adhesive so that the web material upon contact with the creping adhesive disposed upon the surface of the Yankee drum drying system DIICS has a molar ratio of MIICS to DIICS of about less than or equal to 10.

DETAILED DESCRIPTION OF THE INVENTION

Figure 1:
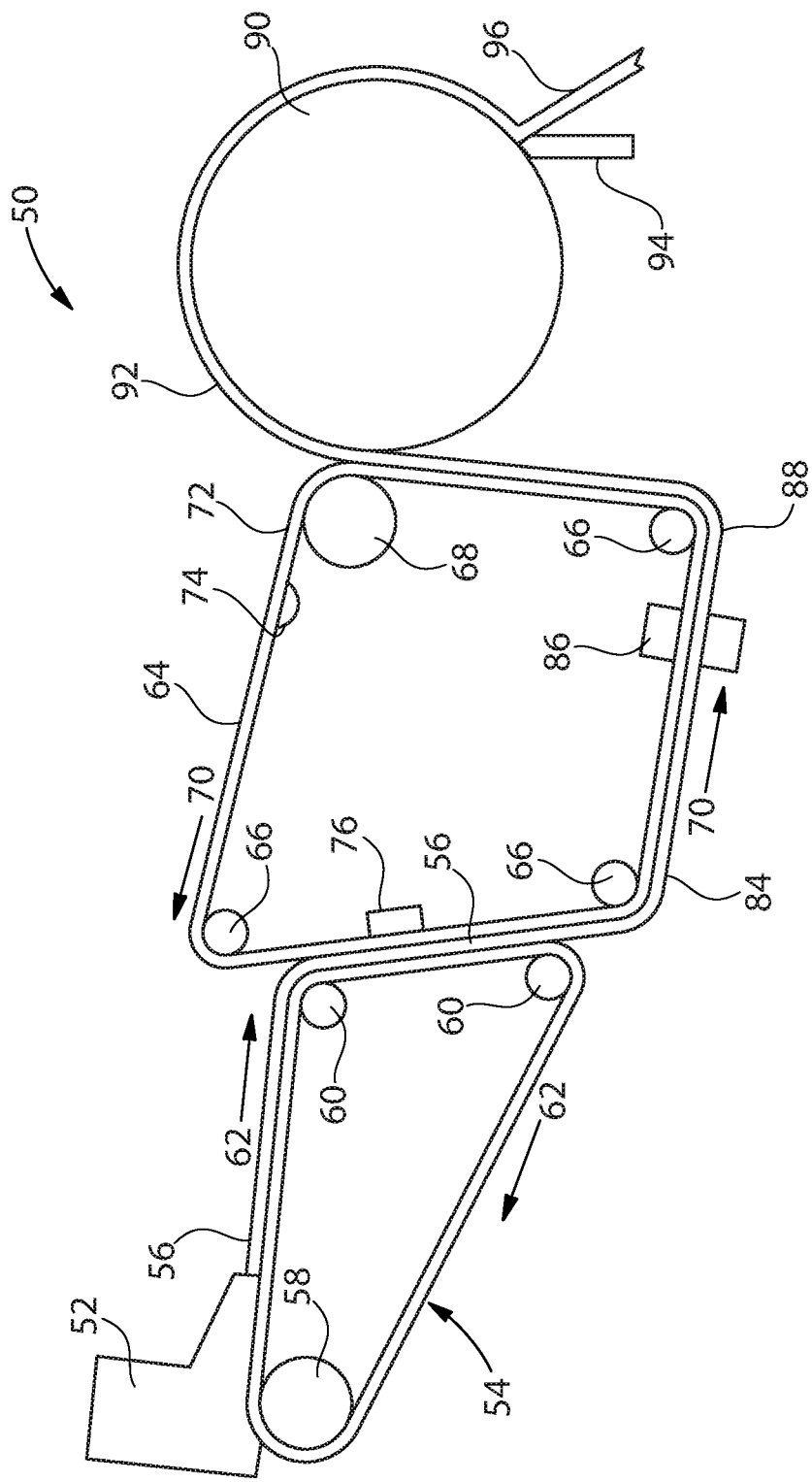
FIG. 1 is a side elevational view of an exemplary papermaking system suitable for use with the present disclosure; and, FIG. 2 is a side elevational view of an exemplary Yankee drying drum system and creping process suitable for use with the present disclosure.

The present disclosure is applicable to creped tissue and towel paper in general and includes but is not limited to conventionally wet pressed creped tissue and towel paper, high bulk pattern densified creped tissue paper and towel and high bulk, uncompacted creped tissue and towel paper.

The present disclosure provides a method to predict when a particular pulp and/or pulp manufacturing process can negatively impact the Yankee dryer adhesive of a tissue and towel manufacturing system. This disclosure also provides a method to proactively manage the Yankee dryer adhesive coating and the impact of inorganic ions present in the web material adhered thereto by proactively managing, adding, and/or controlling the cationic salts present in the fibrous pulp at the pulp manufacturing location, at the wet end of the papermaking operation, or anywhere in the tissue and/or towel manufacturing process (up to and including the Yankee creping adhesive spray booms) to facilitate ion exchange to a favorable molar ratio of monovalent inorganic ionizable cation species to divalent inorganic ionizable cation species of less than or equal to 10. This ion exchange process and mechanism can also be effective for use with PAE based creping adhesives and other Yankee creping adhesive chemistries including polyvinyl alcohols, polyamines, polyvinyl acetates, polyacrylamides, and polyethyleneimines.

The present disclosure also provides a process for manufacturing a tissue and/or towel web material on a papermaking machine having a headbox wet ingredient mixing system and a Yankee drum drying system, wherein the Yankee drum drying system is supplied by a creping adhesive. A divalent inorganic ionizable cation species can be added to the pulp manufacturing or papermaking process to maintain a molar ratio of monovalent inorganic ionizable cation species to divalent inorganic ionizable cation species in the solid phase of the incoming structure to the Yankee dryer is less than or equal to 10. It is believed that this ion exchange process and mechanism is equally effective on PAE based adhesives and other Yankee creping adhesive chemistries including polyvinyl alcohols, polyamines, polyvinyl acetates, polyacrylamides, and polyethyleneimines.

By adding a divalent inorganic ionizable cation species anywhere in the pulp manufacturing or papermaking processes that allows ion exchange when the molar ratio of monovalent ions to divalent ions is greater than 10, it was surprisingly found that Yankee creping adhesive appearance and performance significantly improved from a non-treated state. The improvement in Yankee creping adhesive performance can be measured by increased Yankee creping adhesive appearance and tack, improved creping blade life, improved crepe quality, improved paper machine reliability and improved tissue product attributes.

It was also surprisingly found that the molar ratio of monovalent ions to divalent ions can be measured in the papermaking white water loop, pulper(s), papermaking chests, or other aqueous papermaking and stock streams and used as a predictive tool for Yankee creping adhesive performance and/or for the control of dissolved divalent ion addition to maintain the molar ratio of monovalent inorganic ionizable cation species to divalent inorganic ionizable cation species to less than or equal to 50 in the white water loop, and a molar ratio of monovalent inorganic ionizable cation species to divalent inorganic ionizable cation species to less than or equal to 10 in tissue machine pulper(s), papermaking chests, or other aqueous papermaking and stock streams. These ions can be ionizable into an aqueous solution and therefore be combined with counter ions that are easily dissociated in water.

Papermaking

The web materials for use as tissue and/or towel products made by the techniques described herein can be made by any suitable process known in the art. Such processes can incorporate a cylindrical dryer such as a Yankee dryer.

FIG. 1 is a simplified, schematic representation of an exemplary continuous web material manufacturing process and machine (i.e., a 'papermaking machine') incorporating a Yankee dryer. A process and associated equipment 50 for making a fibrous structure can generally comprise supplying an aqueous dispersion of fibers (a fibrous furnish formed from a papermaking pulp) to a headbox 52 which can be of any convenient design. From the headbox 52, the aqueous dispersion of fibers is delivered to a first foraminous member 54 (a Fourdrinier wire) to produce an embryonic fibrous web 56.

The first foraminous member 54 may be supported by a breast roll 58 and a plurality of return rolls 60 of which only two are shown. The first foraminous member 54 can be propelled in the direction indicated by directional arrow 62 by a drive means (not shown). Optional auxiliary units and/or devices commonly associated fibrous structure making machines and with the first foraminous member 54 can include forming boards, hydrofoils, vacuum boxes, tension rolls, support rolls, wire cleaning showers, and the like.

After the aqueous dispersion of fibers is deposited onto the first foraminous member 54, an embryonic fibrous web 56 is formed by the removal of a portion of the aqueous dispersing medium by techniques well known to those skilled in the art. Vacuum boxes, forming boards, hydrofoils, and the like are useful in effecting water removal. The embryonic fibrous web 56 may travel with the first foraminous member 54 about return roll 60 and is brought into contact with a molding member, such as a deflection member 64, which may also be referred to as a second foraminous member. While in contact with the deflection member 64, the embryonic fibrous web (i.e., web material) 56 can be deflected, rearranged, and/or further dewatered.

The deflection member 64 may be in the form of an endless belt. In this simplified representation, deflection member 64 passes around and about deflection member return rolls 66 and impression nip roll 68 and may travel in the direction indicated by directional arrow 70. Associated with deflection member 64, but not shown, may be various support rolls, other return rolls, cleaning means, drive means, and the like known to those skilled in the art that may be commonly used in fibrous structure making machines.

Regardless of the physical form which the deflection member 64 takes, whether it is an endless belt as just discussed or some other embodiment such as a stationary plate for use in making hand sheets or a rotating drum for use with other types of continuous processes, it must have certain physical characteristics. For example, the deflection member may take a variety of configurations such as belts, drums, flat plates, and the like.

First, the deflection member 64 may be foraminous. That is to say, it may possess passages connecting its first surface 72 (or "upper surface" or "working surface"; i.e. the surface with which the embryonic fibrous web is associated, sometimes referred to as the "embryonic fibrous web-contacting surface") with its second surface 74 (or "lower surface"; i.e., the surface with which the deflection member return rolls are associated). In other words, the deflection member 64 may be constructed in such a manner that when water is caused to be removed from the embryonic fibrous web 56, as by the application of differential fluid pressure, such as by a vacuum box 76, and when the water is removed from the embryonic fibrous web 56 in the direction of the deflection member 64, the water can be discharged from the system without having to again contact the embryonic fibrous web 56 in either the liquid or the vapor state.

Second, the first surface 72 of the deflection member 64 may comprise one or more ridges. The ridges may be made by any suitable material. For example, a resin may be used to create the ridges. The ridges may be continuous, or essentially continuous. The ridges may be arranged to produce the fibrous structures of the present invention when utilized in a suitable fibrous structure making process. The ridges may be patterned. The ridges may be present on the deflection member at any suitable frequency to produce the fibrous structures of the present invention. The ridges may define within the deflection member a plurality of deflection conduits. The deflection conduits may be discrete, isolated, deflection conduits.

The deflection conduits of the deflection member 64 may be of any size and shape or configuration so long as the deflection conduits produce a plurality of line elements in the fibrous structure produced thereby. The deflection conduits may repeat in a random pattern or in a uniform pattern. Portions of the deflection member 64 may comprise deflection conduits that repeat in a random pattern and other portions of the deflection member 64 may comprise deflection conduits that repeat in a uniform pattern. The ridges of the deflection member 64 may be associated with a belt, wire or other type of substrate. The woven belt may be made by any suitable material, for example polyester, known to those skilled in the art.

After the embryonic fibrous web 56 has been associated with the deflection member 64, fibers within the embryonic fibrous web 56 are deflected into the deflection conduits present in the deflection member 64. In one example of this process step, there is essentially no water removal from the embryonic fibrous web 56 through the deflection conduits after the embryonic fibrous web 56 has been associated with the deflection member 64 but prior to the deflecting of the fibers into the deflection conduits. Further water removal from the embryonic fibrous web 56 can occur during and/or after the time the fibers are being deflected into the deflection conduits. Water removal from the embryonic fibrous web 56 may continue until the consistency of the embryonic fibrous web 56 associated with deflection member 64 is increased to from about 25% to about 35%. Once this consistency of the embryonic fibrous web 56 is achieved, then the embryonic fibrous web 56 is referred to as an intermediate fibrous web 84. During the process of forming the embryonic fibrous web 56, sufficient water may be removed, such as by a noncompressive process, from the embryonic fibrous web 56 before it becomes associated with the deflection member 64 so that the consistency of the embryonic fibrous web 56 may be from about 10% to about 30%.

Any convenient means conventionally known in the papermaking art can be used to dry the intermediate fibrous web 84. Examples of such suitable drying process include subjecting the intermediate fibrous web 84 to conventional (vacuum/press drying) and/or air flow-through dryers and/or Yankee dryers. Tissue and Towel webs may be one density or may be formed to have multiple densities.

In one example of a drying process, the intermediate fibrous web 84 in association with the deflection member 64 passes around the deflection member return roll 66 and travels in the direction indicated by directional arrow 70. The intermediate fibrous web 84 may first pass through an optional pre-dryer 86. This pre-dryer 86 can be a conventional flow-through dryer (hot air dryer) well known to those skilled in the art. Optionally, the pre-dryer 86 can be a socalled capillary dewatering apparatus. In such an apparatus, the intermediate fibrous web 84 passes over a sector of a cylinder having preferential-capillary-size pores through its cylindricalshaped porous cover. Optionally, the pre-dryer 86 can be a combination capillary dewatering apparatus and flow-through dryer. The quantity of water removed in the pre-dryer 86 may be controlled so that a pre-dried fibrous web 88 exiting the pre-dryer 86 has a consistency of from about 30% to about 98%. The pre-dried fibrous web 88, which may still be associated with deflection member 64, may pass around another deflection member return roll 66 and as it travels to an impression nip roll 68. As the pre-dried fibrous web 88 passes through the nip formed between impression nip roll 68 and a surface of a Yankee dryer 90, the ridge pattern formed by the top surface 72 of deflection member 64 is impressed into the pre-dried fibrous web 88 to form a line element imprinted fibrous web 92.

The imprinted fibrous web 92 can then be adhered to the surface of the Yankee dryer 90 where it can be dried to a consistency of at least about 95%. The imprinted fibrous web 92 can then be foreshortened by creping the imprinted fibrous web 92 with a creping blade 94 to remove the imprinted fibrous web 92 from the surface of the Yankee dryer 90 resulting in the production of a creped fibrous structure 96 in accordance with the present invention. The creped fibrous structure 96 may be subjected to post processing steps such as calendaring, tuft generating operations, and/or embossing and/or converting.

The fibrous structure may be incorporated into a single- or multi-ply sanitary tissue product. The sanitary tissue product may be in roll form where it is convolutedly wrapped about itself with or without the employment of a core. In one example, the sanitary tissue product may be in individual sheet form, such as a stack of discrete sheets, such as in a stack of individual facial tissue.

Yankee Dryer

Figure 2:
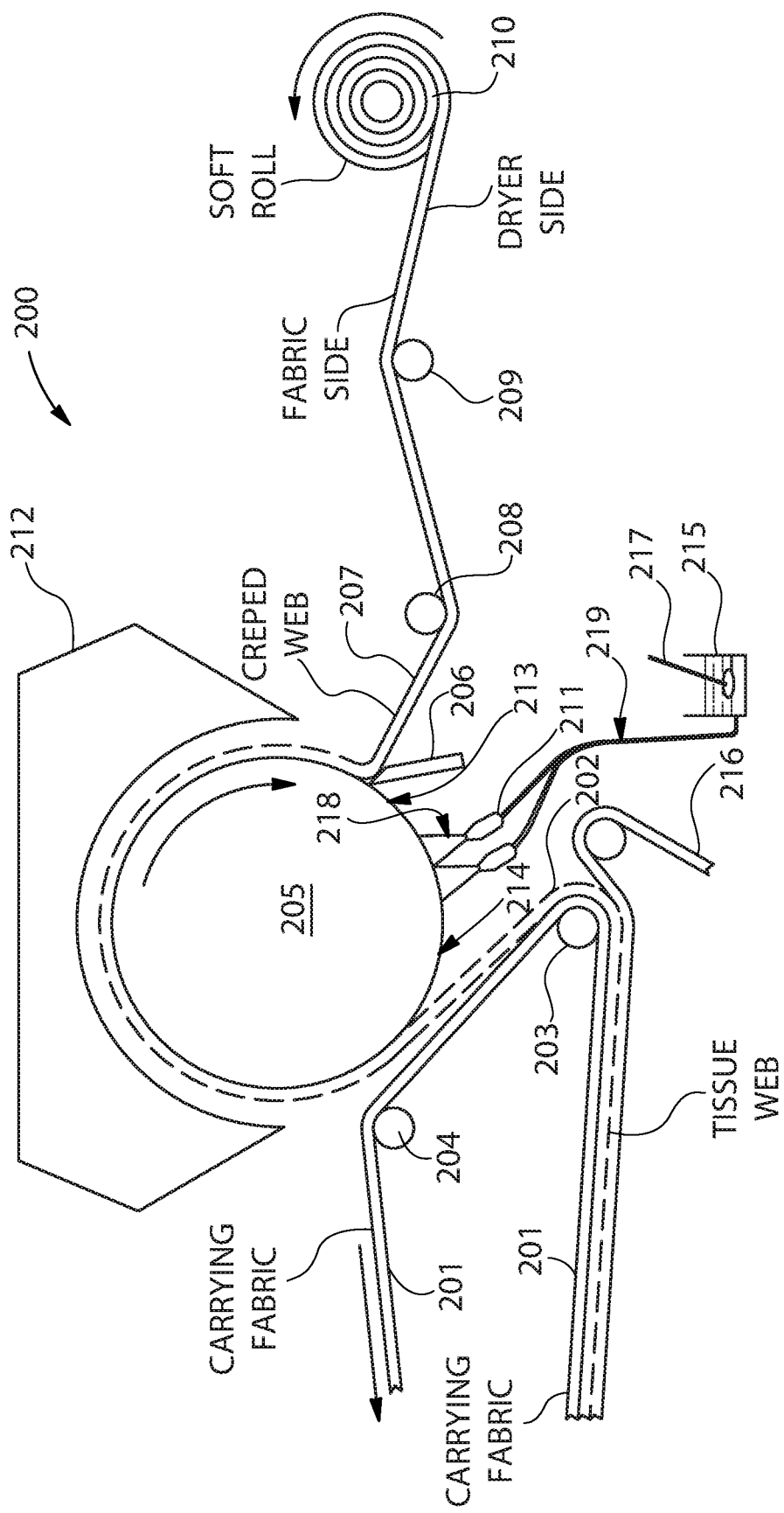

FIG. 2, shows an example of a standard process for the final drying and creping of a web material using a Yankee dryer. In this example, the tissue web is brought to the Yankee dryer on a flat, wire, fabric or belt and pressed to the Yankee dryer 205. The web material being dried by the Yankee dryer may have an incoming moisture content ranging from 10% to 90%. Further, this moisture may not be uniform within the sheet by design, especially using current structured papermaking technologies.

The creping adhesive can be applied to the surface of the Yankee dryer 205 via spray nozzles. The transfer and impression fabric 201 can carry the formed, dewatered and partially dried web material 202 around turning roll 203 to the nip between press roll 204 and Yankee dryer 205. A supplemental lower carrier 216 may also be employed to carry the web material in a sandwich fashion, which may be particularly useful under conditions of higher web dryness. The fabric 201, web material 202, and Yankee dryer 205 move in the directions indicated by the arrows. Once pressed to the Yankee dryer 205, the web material 202 is carried on the Yankee dryer 205 around the roll to the creping blade 206 which crepes the traveling web material 202 from the surface of the Yankee dryer 205 as indicated at 207. The creped web material 207 exiting from the Yankee dryer 205 then passes over guide and tension rollers 208, 209 and is wound into a soft creped tissue roll 210.

To adhere a partially dried and dewatered paper web material 202 (e.g., a 10-90 wt. % fiber consistency) entering the Yankee dryer 205 to the surface of the Yankee dryer 205, a spray boom 211 can be used to apply a creping adhesive composition 218 to the dryer surface 213 which is exposed after the creped tissue web 207 is removed from the dryer 205 to provide an adhesive dryer surface 214 ahead of the nip between the press roll 204 and Yankee dryer 205. The spray boom 211 can be a single spray boom or multi-spray boom, such as a dual-spray boom as illustrated. The spray boom can include an overspray collection container (not shown). The spray boom 211 is fluidly connected 219 to a mixing pot 215 for feeding creping adhesive composition from the mixing pot. The mixing pot 215 can be equipped with an agitator 217.

The creping adhesive of the present invention can comprise the standard materials for creping adhesives such as adhesion glue, creping modifiers and release modifiers. Creping adhesive may also comprise an aqueous stream containing divalent cations that can be introduced into the mixing pot 215 in any convenient manner. The resulting creping adhesive can be pumped or otherwise fed under pressure to the nozzle sprayer(s) of the spray boom 211. To promote drying of the web on the dryer, the Yankee dryer 205 can be internally steam heated by conventional or other suitable arrangements (not shown), externally heated using a hood 212, or using both. This sprayed composition 218 optionally may be applied to the traveling web 202 directly. However, it may be directly sprayed onto the dryer surface 213 to limit the pickup of adhesive by the web material 202 and to limit the penetration of adhesive through the web material 202 to the carrying fabric.

Papermaking Materials

The terms "fibrous structure", "fibrous web", "web material", and similar terms as used herein refer to a fibrous material that may be comprised of cellulosic and non-cellulosic components. These wood pulp-based cellulosic and non-cellulosic components can include papermaking fibers and other various additives that are mixed with water to form an aqueous slurry. This aqueous slurry constitutes the aqueous papermaking furnish. It is anticipated that wood pulp in all its varieties will normally comprise the papermaking fibers. However, other cellulose fibrous pulps, such as cotton linters, bagasse, rayon, etc., can be used and none are disclaimed. Wood pulps can also include chemical pulps such as, sulfite and sulfate (sometimes called Kraft) pulps as well as mechanical pulps including for example, groundwood, thermomechanical pulp (TMP) and chemithermomechanical pulp (CTMP).

Both hardwood pulps and softwood pulps as well as combinations of the two may be employed as papermaking fibers. The term "hardwood pulps" as used herein refers to fibrous pulp derived from the woody substance of deciduous trees (angiosperms), whereas "softwood pulps" are fibrous pulps derived from the woody substance of coniferous trees (gymnosperms). Pulps from both deciduous and coniferous trees can be used. Blends of hardwood Kraft pulps, especially eucalyptus, and northern softwood Kraft (NSK) pulps are particularly suitable for making the tissue webs of the present invention. One of skill in the art will recognize that layered tissue webs that form tissue and towel products can utilize hardwood pulps such as eucalyptus for outer layer(s) and northern softwood Kraft pulps for the inner layer(s).

Other additives can be added to an aqueous papermaking furnish or the fibrous structure to impart characteristics to the resulting paper product or improve the papermaking process. This can include the addition of a cationic strengthening polymer to the papermaking furnish. Generally, cationic strengthening polymers may be applied in various amounts, depending on the desired characteristics of the resulting web material. For instance, total wet strength agents between about 0.5 to 50 kg/T can be added. These strength polymers can be incorporated into any layer of a multi-layer tissue web. A cationic strengthening polymer can be a cationic water-soluble resin such as polyamide epichlorohydrin (PAE), urea-formaldehyde resins, melamine formaldehyde resins, polyacrylamide resins, dialdehyde starches, and mixtures thereof.

A "wet strength agent" is a material that when added to pulp fibers provides a resulting web material with a wet geometric tensile strength to dry geometric tensile strength ratio in excess of about 0.1. Typically, these are termed either "permanent" wet strength or "temporary" wet strength agents. Such temporary and permanent wet strength agents may also sometimes function as dry strength agents to enhance the final tissue and/or towel product strength when dry.

The strength additive may be selected from the group consisting of permanent wet strength resins, temporary wet strength resins, dry strength additives, and mixtures thereof. If permanent wet strength resins include polyamide epichlorohydrin, polyacrylamides, insolubilized polyvinyl alcohol, urea formaldehyde, polyethyleneimine, and chitosan polymers. If temporary wet strength is desired, a suitable additive can be a cationic dialdehyde starch-based resin and dialdehyde starch, and modified polyacrylamide resins. If dry strength is desired, a suitable additive can be a polyacrylamide, starch (such as corn starch or potato starch), polyvinyl alcohol (guar or locust bean gums), and/or carboxymethyl cellulose.

These wet and dry strength resins may be added to the pulp furnish in addition to being added by the process described in this disclosure. It is to be understood that the addition of chemical compounds such as the wet strength and temporary wet strength resins discussed above to the pulp furnish is optional and is not necessary for the practice of the present development.

Papermaking Pulp Fiber Chemistry

It has been discovered that a wood pulp (chemical or mechanical) with a molar ratio higher than 10 of the molar amount of monovalent ions to the molar amount of divalent ions (by way of non-limiting example—$[Na^+]/[Ca^{+2}]$, $[Na^+]/$ $[Mg^{+2}]$, $[Na^+]/[Ca^{+2}+Mg^{+2}]$, or represented in general as $[Na^+]/[X^{+2}]$ where X is sum of all divalent ions) has difficulty running on tissue/towel/paper machines due to an observed lower pH, negative interactions with tissue/towel Yankee creping adhesive reliability and tack, and interferes with fiber-to-fiber bonding. Furthermore, it has also been discovered that the papermaking white water system with a molar ratio of monovalent to divalent ions greater than or equal 50 will also present similar difficulties.

As would be understood by one of skill in the art, a "molar ratio" is defined as the ratio of the amount of moles of a given substance or element in a compound (solid, liquid, and/or gas) by the amount of moles of a second given substance or element in the same compound. For the instant description the molar ratio is the ratio of the amount of monovalent ions to the amount of divalent ions. In this example, the amount of moles of monovalent ions (e.g., typically $Na^+$) to the amount of moles of divalent ions (e.g., typically $Ca^{+2}$) can be determined by the molar content of such ions present in papermaking raw fibrous pulp, paper stock, web material or process water and/or filtrates.

Those skilled in the art understand that a tissue and/or towel papermaking process is a highly complex operation. This highly complex operation can be significantly effected by minute changes in the pulp raw materials used to supply the papermaking fibers and/or any changes in the water quality used in the entirety of the papermaking process (for example pH). This necessarily includes the papermaking fibers and water that are fed to any re-pulpers and then ultimately to the paper machine. Impacts on the paper machine caused by these raw material changes (e.g., water and/or pulp) can have a drastic impact on the finally produced web product and can be manifest to virtually all different areas of the paper machine. For example, final web material product defects and the causation can include but not be limited to an increased number of holes in the finally produced tissue and/or towel fibrous web that is caused by buildup of sticky material on the creping blade or seal rolls throughout the papermaking process.

This raw material variability can require an increase in creping blade changes required to keep any final web material product parameters within specification. Further, raw material variability can cause an increase in the thickness, and a change in the material hardness of, the Yankee creping adhesive resulting in a required increase of cleaning blade changes, increased creping blade changes, increased tissue sheet strength variability, increased variability of creping on sheet properties, and/or increased sheet breaks. Additionally, one of skill in the art will readily recognize that material variability can also result in a change in the Yankee creping adhesive coating glass transition properties that can result in poor sheet tack (i.e., either too weak or too strong making it difficult to crepe) to the Yankee drier, a noticeable sticky material buildup on seal rolls associated with the through air drying process, a sticky material buildup on piping and chests that can be released as a result of a pH change of 1 or more units, and/or a step-change in water temperature or other system shock or high shear. Surprisingly, it was discovered that these issues were related to the molar ratio of monovalent inorganic ionizable cation species to divalent ionizable cation species discussed herein in detail.

Furthermore it was surprisingly discovered that a molar ratio of monovalent inorganic ionizable cation species (e.g., Lithium ($Li^+$), sodium ($Na^+$), Potassium ($K^+$) and Rubidium ($Rb^+$), counter ions, source salts, oxides, derivatives, and combinations thereof) to divalent inorganic ionizable cation species (e.g., beryllium ($Be^{+2}$), magnesium ($Mg^{+2}$), calcium ($Ca^{+2}$), strontium ($Sr^{+2}$), barium ($Ba^{+2}$), radium ($Ra^{+2}$), counter ions, source salts, oxides, derivatives, and combinations thereof) of higher than about 10 creates the observed difficulties with the Yankee dryer creping process and the observed defects in the resulting creped web material. Also, it was surprisingly discovered that a molar ratio of monovalent to divalent ions of lower than about 0.1 similarly creates these observed difficulties with the Yankee dryer creping process and the observed defects in the resulting creped web material. In this regard, it was found that the addition or the reduction of monovalent and/or divalent ionizable compounds within the pulp manufacturing process or within the papermaking process (i.e., to the papermaking machine) to maintain a molar ratio of monovalent ions to divalent ions in the solid phase of the incoming structure to the Yankee drier of about less than or equal to 10 and greater than about 0.1 can reduce these observed negative attributes of the web material removed from the surface of the Yankee dryer. One skilled in the art would appreciate that the molar ratio of monovalent to divalent ions can be less than or equal to 10, or can range from about 0.1 to about 10, or from about 1 to about 9, or about 2 to about 7, or from about 4 to about 6, or be about 5.

It has been surprisingly found that the modification of the monovalent ion to divalent ion molar ratio can be accomplished by adding divalent inorganic ionizable cationic species or removing monovalent inorganic ionizable cationic species (also called "MIICS" herein) within the papermaking process to drive the monovalent to divalent molar ratio to less than or equal to 10. Further, adding divalent inorganic ionizable cationic species (also called "DIICS" herein) or removing MIICS can occur in the pulp making operation to drive the monovalent to divalent molar ratio to less than or equal to 10. Also, the addition of DIICS or removal of MIICS can occur in the pulp bleaching process section as well as the brown stock washing process section to drive the monovalent to divalent molar ratio to less than or equal to 10. Finally, one of skill in the art will recognize that adding DIICS or removing MIICS can be accomplished anywhere in the pulp mill water system (washing water system and/or the fresh water feed to the pulping operation) or within the papermaking water system so that final pulp fiber ion content and the ionic molar ratio discussed supra, provide a monovalent to divalent molar ratio of less than or equal to 10.

As mentioned, the addition of DIICS or the removal MIICS can occur at any point ranging from the production of wood pulp fibers at the pulp mill to the creping blade removing the adhesively connected web material from the surface of the Yankee dryer. The techniques and locations within the papermaking process are discussed infra. This includes discrete discussion related to the locations and techniques suitable for the addition of DIICS across the pulp and papermaking processes as well as the locations and techniques suitable for the removal MIICS across the pulp and papermaking processes.

1. Addition of Divalent Inorganic Ionizable Cationic Species a. Adding Divalent Inorganic Ionizable Cationic Species to the Pulp Making Process or Pulp Mill In one example of the processes of the present disclosure is the embodiment where divalent inorganic ionizable cationic species (DIICS) (e.g., $Ca^{+2}$) are added in the pulp production process (Kraft, chemithermomechanical, semi-bleached, thermomechanical, or bio-pulping processes), either in solid state or pre-slurried and pumped. This can be done preferably but not limited to the last stages in pulp production process such as bleaching, washing and drying operations—tanks, chests, pipelines, pumps or any auxiliary equipment that is part of such processes. It may also be done directly (by incorporating such divalent cations salts and/or oxides) on the pulp sheet (during or after sheet formation, before or after drying) or in the stock flow, or indirectly through side streams of water and filtrates (such as recirculating white water, fresh water streams, and the like). Other embodiments include the use of compounds where the divalent cations are coupled with the following anions: acetate, formiate, carbonate, bicarbonate, nitrite, sulphate, chloride, fluoride, bromide, and iodine. The target for the addition of DIICS is to ensure the ratio of monovalent inorganic ionizable cationic species MIICS (e.g., $Na^+$) to DIICS (e.g., $Ca^{+2}$) is less than or equal to 10.

To determine the molar ratio of MIICS to DIICS, the pulp production process can incorporate the use of a MIICS measuring device and a DIICS measuring device. As the pulp material is manufactured, the molar concentration of the MIICS can be measured in discrete time periods, or even continuously, with the MIICS measuring device. Similarly, the molar concentration of the DIICS can be measured in discrete time periods, or even continuously, with the DIICS measuring device. Based upon the data collected by the MIICS and DIICS measuring devices, the molar ratio of the measured molar concentration of MIICS to the measured molar concentration of DIICS can be calculated. This ratio can then be compared to the desired MIICS to DIICS ratio of about less than or equal to 10. If the calculated molar ratio in the web material is greater than 10 in the web material, then an amount of DIICS can be added to the pulp manufacturing process.

Additionally, the ratio of MIICS to DIICS can be determined in the final pulp material produced by the pulp production process. This can result in the manufacture of saleable pulp product suitable for use in a papermaking process that results in the beneficial production of web material by the papermaking process that has reduced observed defects as discussed supra. Here, the molar ratio of MIICS to DIICS in the finally produced pulp product can be determined by a quantitative ashing process. The ashed pulp product can then be measured for the respective concentration of MIICS and DIICS. By way of non-limiting example, the final pulp product produced by the pulp making process can be ashed by following any of several different standards, namely but not limited to: ISO 1762:2015, ISO/DIS 1762, Tappi T211 om-02, Scan C06, ASTM d586-97, AS/NZ 1301.418, ISO 2144, NBRNM-ISO2144, ABNT NBR 13999:2017, IS 6213 (p.VII):2012, among others. The ashed product can then be measured for MIICS and DIICS molar content by a technique that enables the quantitative analysis of ions such as Atomic Absorption Spectroscopy, Ion Chromatography, Inductively Coupled Plasma with Mass Spectroscopy (ICP-MS), Inductively Coupled Plasma with Optical Emission Spectroscopy (ICP-OES), and the like.

Based upon the analysis of the ashed pulp product, the molar ratio of MIICS to DIICS can then be compared to the desired MIICS to DIICS ratio of about less than or equal to 10. If the calculated molar ratio in the web material is greater than 10 in the pulp product, then an amount of DIICS can be added to the pulp manufacturing process.

b. Addition of DIICS to the Pulper

One skilled in the art can contemplate the addition of DIICS directly to the paper machine thick stock pulp system either in the paper machine stock preparation pulper or into any one of the pulp slurry lines, either in solid form of salts being added in conjunction with water to the pulper or via a pre-slurried mixture that is pumped and metered into pulp stock lines to obtain the desired ratio of monovalent ions to divalent ions is less than or equal to 10. Furthermore, other embodiments include the use of compounds where the DIICS are coupled with anions such as acetate, formiate, carbonate, bicarbonate, nitrite, sulphate, chloride, fluoride, bromide, and iodine. In any regard, the target for the addition of divalent ions or removal of monovalent ions is to ensure the ratio of MIICS to DIICS is less than or equal to 10.

It should be understood by one of skill in the art that the molar content of MIICS and DIICS in any portion of a papermaking process (each discussed infra) where the papermaking fibers exist in an aqueous state can be measured with the use of a MIICS measuring device and a DIICS measuring device. As the web material is manufactured by the papermaking machine, the molar concentration of the MIICS can be measured in discrete time periods, or even continuously, with the MIICS measuring device. Similarly, the molar concentration of the DIICS can be measured in discrete time periods, or even continuously, with the DIICS measuring device. Based upon the data collected by the MIICS and DIICS measuring devices, the molar ratio of the measured molar concentration of MIICS to the measured molar concentration of DIICS can be calculated. This ratio can then be compared to the desired MIICS to DIICS ratio of about less than or equal to 10. If the calculated molar ratio in the web material is greater than 10 in the web material, then an amount of DIICS can be added to the papermaking process.

c. Adding DIICS to the Thick Stock Feed to the Paper Machine.

A second example of the processes of the present disclosure is the embodiment DIICS are added directly to the paper machine thick stock pulp slurry, either in solid state or pre-slurred and pumped. Other embodiments can include the use of compounds where the DIICS are coupled with the following anions: acetate, formiate, carbonate, bicarbonate, nitrite, sulphate, chloride, fluoride, bromide, and iodine. The target for the addition of divalent ions is to ensure the ratio of monovalent ions to divalent ions in the paper machine thick stock pulp slurry is less than or equal to 10.

As discussed supra, the molar content of MIICS and DIICS in the paper machine thick stock pulp slurry can be measured with the use of a MIICS measuring device and a DIICS measuring device. The molar ratio of MIICS to DIICS present in the paper machine thick stock pulp slurry can be determined as discussed supra.

d. Adding DIICS to the Papermaking Process

Another example of the processes of the present disclosure provides for the addition of DIICS to the papermaking fibers present in the tissue and towel papermaking process. Suitable tissue and towel papermaking processes can include, but not be limited to, conventional dry crepe processes, the Voith® ATMOS® process, the Valmet® NTT® process, the Valmet® NTTQRT® process, the Andritz® TEX® process, various through-air-dried process, or any other crepe tissue production process available and/or envisioned. It is believed that DIICS can be delivered at any point within the paper or tissue production process, either in solid state or pre-slurried and pumped to approach flow tanks, pipes, pumps or any other devices before and up to and including the paper machine headbox. Other embodiments can include the use of compounds where the DIICS are coupled with the following anions: acetate, formiate, carbonate, bicarbonate, ni*trite*, sulphate, chloride, fluoride, bromide, and iodine. The target for the addition of DIICS to the papermaking fibers present in the tissue and towel papermaking process is to ensure the molar ratio of MIICS to DIICS in the papermaking fibers present in the tissue and towel papermaking process is less than or equal to 10.

As discussed supra, the molar content of MIICS and DIICS in the aqueous paper fibers present within the paper machine can be measured with the use of a MIICS measuring device and a DIICS measuring device. The molar ratio of MIICS to DIICS present the aqueous paper fibers present within the paper machine can be determined as discussed supra.

e. Papermaking Machine Fresh or Make-Up Water:

Another example of the processes of the present disclosure provides for the addition of DIICS to the tissue and towel papermaking process via the papermaking fresh or make-up water system. Adding ionizable cations can change the character and/or hardness of the paper machine water such that it has excess DIICS available to ion exchange with the pulp to achieve the target ratio of MIICS to DIICS of less than or equal to 10.

As discussed supra, the molar content of MIICS and DIICS in the papermaking fresh or make-up water system can be measured with the use of a MIICS measuring device and a DIICS measuring device. The molar ratio of MIICS to DIICS present the papermaking fresh or make-up water system can be determined as discussed supra.

One of skill in the art will also recognize that the molar content of MIICS and DIICS in the water streams can also be determined by a quantitative ashing process such as those described herein) followed by any quantitative analytical technique that enables the quantitative analysis of ions such as AA, ICP-MS, IC, ICP-OES, among others (also discussed previously herein).

f. Papermaking Machine White Water

In yet another example of the processes of the present disclosure DIICS can be added indirectly through side streams of water and filtrates (such as recirculating white water, papermaking water treatment processes and shower makeup water sources) used in the tissue or paper machine. It was surprisingly found that the ratio for this method of application of DIICS was different from that observed in pulp addition to affect the same impact on the tissue papermaking creping adhesive system reliability. Here, it is preferred that the molar ratio of MIICS to DIICS is less than or equal to 50 versus the pulp target of less than or equal to 10. The molar ratio of MIICS to DIICS in the water circuit is higher due to differences in mass balance and the ion-exchange reactions taking place with the pulp, as well as to avoid scaling and its undesired side effects in the paper machine.

As discussed supra, the molar content of MIICS and DIICS in the papermaking machine white water system can be measured with the use of a MIICS measuring device and a DIICS measuring device. The molar ratio of MIICS to DIICS present the papermaking machine white water system can be determined as discussed supra.

One of skill in the art will also recognize that the molar amounts of MIICS and/or DIICS to be added into the streams may also be estimated by material balance after a preliminary quantitative analysis.

g. Spraying DIICS onto a Surface of the Web Material Prior to Contact with the Yankee Dryer In yet another example of the processes of the present disclosure provides for the addition of DIICS done directly through the application of a concentrated mixture of DIICS via a topical application to the web material prior to the web material being pressed to the Yankee dryer for final drying and creping. One skilled in the art can envision a spray, weir, roll or other system to apply a metered amount of divalent ions to the surface of the paper before the sheet contacts with Yankee dryer and creping adhesive mixture thereby improving the adhesion of the sheet to the Yankee dryer. The adhesion profile modification can be reached either by changes in adherence, durability or thickness of the adhesive chemical layer to the surface of the Yankee dryer by the modification imparted by the controlled ratio of MIICS to DIICS.

The molar content of MIICS and DIICS present in the web material can be measured with any equipment understood and known to those of skill in the art for measuring the molar content of MIICS and DIICS. The molar ratio of MIICS to DIICS present the papermaking machine white water system can be determined as discussed supra.

h. Addition of DIICS to the Yankee Creping Adhesive Composition

As indicated, the addition of DIICS to the creping adhesive composition 218 may be accomplished by adding soluble salts and/or an aqueous stream containing a concentrated mixture of dissolved cations, which can be diluted, such as on site of the creping location in a mix pot or in line with other materials that are to be sprayed on the cylindrical dryer or even indirectly to the pre-dried sheet between points 202 and 204 as illustrated in FIG. 2.

For example, DIICS can be either in solid state or pre-slurried and added in the tissue production process directly into the creping adhesive composition dilution/make-up tanks. One skilled in the art can envision altering the ionic character of any component of a multicomponent glue system such that the creping adhesive ensures that the interface of the creping adhesive/tissue sheet has a ratio of MIICS to DIICS of less than or equal to 10. Therefore, it is contemplated that the desired MIICS to DIICS molar ratio can be accomplished through a change in the make-up solution for the creping adhesive, the creping adhesive components, or other additive (such as creping or release aids) such that the final creping adhesive mixture has excess ionized DIICS that are able to modify the Yankee coating performance as provided by any of the known and/or understood ion-exchange models with fibers as they contact the Yankee dryer surface. Without desiring to be bound by theory, it is believed that this would mimic the Dreshfield effect that happens with the ion-exchange pulp but, at this point, the ratio of MIICS to DIICS is directly introduced at the edge of the sheet and the Yankee dryer surface.

The addition of DIICS to the creping adhesive composition 218 may require the installation of a device to spray the divalent ions stream at this point, what is not typically present. With the use of the adhesive formulations of the present invention, a superior balance of adhesion and release properties of the fiber web from the surface of a dryer or TAD fabric can be achieved. Comparable or better tack profiles using a biodegradable additive at lower use rates of conventional polyvinyl alcohol creping adhesives (PVOH) or wet strength resins can be obtained with adhesive formulations of the present invention. Further, the adhesive formulation of the present disclosure can be used in other applications of the paper industry or other industries. The adhesive formulation of the present invention can be considered biodegradable, and/or non-toxic, and/or contains one or more food-grade components. The target for the addition of DIICS is to ensure the ratio of MIICS to DIICS is less than or equal to 10.

The molar content of MIICS and DIICS present in the creping adhesive composition 218 can be measured with any equipment understood and known to those of skill in the art for measuring the molar content of MIICS and DIICS. The molar ratio of MIICS to DIICS present the creping adhesive composition 218 can be subsequently determined as discussed supra.

i. Addition of DIICS to the Yankee Creping Adhesive Composition Continuously to the Yankee Drum or Web Material The addition of DIICS can be provided directly to the Yankee dryer surface by a dedicated stream of a slurry containing DIICS sprayed onto the surface of the Yankee dryer by a dedicated spray boom or indirectly by means of a stream, say spraying, onto the tissue sheet or the fabrics in the tissue machine positioned prior to the Yankee dryer. The target is to ensure the ratio of MIICS to DIICS is less than or equal to 10.

Alternatively, the addition of DIICS can be provided directly to the Yankee dryer surface by a dedicated stream of a slurry containing DIICS by a roll application system to ensure that the presence of ionizable divalent cationic species of the creping adhesive prior to sheet contact is sufficient to provide a ratio of MIICS to DIICS that is less than or equal to 10.

The molar content of MIICS and DIICS present in the creping adhesive composition 218 provided directly to the Yankee dryer surface can be measured with any equipment understood and known to those of skill in the art for measuring the molar content of MIICS and DIICS. The molar ratio of MIICS to DIICS present the creping adhesive composition 218 directly to the Yankee dryer surface can be subsequently determined as discussed supra.

Alternatively, the molar content of MIICS and DIICS present in the web material prior to contact with the Yankee dryer surface can be measured by an ashing process according to any of ISO 1762:2015, ISO/DIS 1762, Tappi T211 om-02, Scan C06, ASTM d586-97, AS/NZ 1301.418, ISO 2144, NBRNM-ISO2144, ABNT NBR 13999:2017, and IS 6213 (p.VII):2012. The ashed web material can be measured for the respective concentration of MIICS and DIICS. The ashed web material can then be measured for MIICS and DIICS molar content by a technique that enables the quantitative analysis of ions such as Atomic Absorption Spectroscopy, Ion Chromatography, Inductively Coupled Plasma with Mass Spectroscopy (ICP-MS), Inductively Coupled Plasma with Optical Emission Spectroscopy (ICP-OES), and the like. The molar ratio of MIICS to DIICS present in the web material being applied to the Yankee dryer surface can be subsequently determined as discussed supra. DIICS can then be provided directly to the Yankee dryer surface by a dedicated stream of a slurry containing DIICS by any known application system to ensure that the presence of ionizable divalent cationic species of the creping adhesive prior to sheet contact is sufficient to provide a ratio of MIICS to DIICS that is less than or equal to 10.

One of skill in the art will also recognize that the MICCS to DICCS molar ratio can also be adjusted following a material (or molar) balance calculation and incoming flow balance and sheet or water stream composition.

2. Removal of Monovalent Inorganic Ionizable Cationic Species (MIICS)

It has also been surprisingly found that the modification of the monovalent ion to divalent ion molar ratio can be accomplished by removing MIICS within the pulp making and/or papermaking process to drive the MIICS to DIICS molar ratio to less than or equal to 10. The removal of MIICS can occur at any point ranging from the production of the wood pulp fibers to form the raw pulp material for a papermaking process at the pulp mill through the wet-end of the papermaking process. The techniques and locations within the entirety of the pulp and papermaking processes are discussed infra. This includes discussions related to the discrete locations and techniques suitable for the removal of MIICS across the entire pulp and papermaking processes.

a. Reverse Osmosis

A reverse osmosis process suitable for use with the present disclosure will push water through a membrane with a high-pressure pump to remove a contaminant (here the contaminant is MIICS). Here, the removal of MIICS from any pulp or papermaking process water can be suitably provided at a level to drive the MIICS to DIICS molar ratio to less than or equal to 50. In the present system, the amount of pressure to force water across the semi-permeable membrane in a reverse osmosis system will depend on how saturated the feed water is with MIICS. The higher the MIICS concentration, the more pressure will be needed to overcome the natural osmotic pressure. When adequate pressure is applied, water molecules can pass through the reverse osmosis membrane and the contaminants (i.e., MIICS) can be discharged. The contaminated water containing MIICS can then be drained away or used as feed water and passed through the reverse osmosis system again for further cleansing.

In accordance with the present disclosure, a reverse osmosis system can be installed to remove excess MIICS from any of the water recovery process related to pulp making and/or from the paper machine white water. A reverse osmosis system suitable for the removal of MIICS can be highly desirable for use with paper machines that utilize a partially or even a highly closed water loop system. In any regard, the set-point of MIICS removal is positioned to drive the MIICS to DIICS molar ratio to less than or equal to 50 for the relevant water stream.

b. Distillation

A distillation process suitable for use with the present disclosure can utilize temperature changes to evaporate and re-condense water from a recovery process related to pulp making and/or from the paper machine white water. It has been surprisingly found that inorganic minerals such as MIMICS do not usually transfer into the condensed water. The removal of MIICS from the respective process water is provided at a suitable level to drive the MIICS to DIICS molar ratio to less than or equal to 50.

By way of non-limiting example, a distillation column system can be installed to purify the water in a closed water loop of a paper machine. It was found that this distillation process can remarkably reduce the amount of dissolved MIICS present within the water loop. As the water steam in the distillation column condenses with virtually no concentration of MIICS disposed therein, one of skill in the art could then also add DIICS in order to provide a MIICS to DIICS molar ratio the treated process water of less than or equal to 50.

c. Ion Exchange—Substitution of DIICS by MIICS and/or Substitution of MIICS by DIICS.

Molecular sieves can be either natural or synthetic materials with regular and uniform pore sizes and a high surface area and having an internal channel structure that is capable of separating molecules of different dimensions. By way of example, zeolites are a class of molecular sieves that have a crystalline structure composed of aluminosilicate (occasionally doped with other metals). This structure provides cavities that can be occupied by large cations and water molecules thereby presenting high adsorption capacity. Molecular sieves can be used as catalysts (directly or as support for catalysts), adsorbents, and/or ion-exchange resins. The incorporation of aluminum in the silicate structure can result in an anionic character that can be neutralized by cations such as calcium, sodium or potassium.

It is well understood by those skilled in the art of physical chemistry, inorganic chemistry, and/or materials science that molecular sieves can be used to soften hard water. This is achieved by means of using a MIICS form of molecular sieve in a DIICS-rich water environment. Here, the molecular sieve can trap MIICS and release DIICS to the water, resulting in a decreased hardness level. The removal of MIICS from process water can be provided at a suitable level to drive the MIICS to DIICS molar ratio to less than or equal to 50.

Not being bound to the theory, we envision that the present disclosure can make use of molecular sieves to selectively increase the concentration of DIICS, or MIICS, in such a way that the required molar ratio of MIICS to DIICS of less than or equal to 50 in the liquid phase or less than 10 in the fibrous (i.e., solid) phase of the pulp and/or papermaking process is met. In any regard, as discussed supra, the addition of DIICS and/or the trapping/removal of MIICS anywhere in the pulp and/or papermaking process by means of such an ion exchange can improve the performance from a non-treated state.

For example, a treatment can be accomplished by direct addition of DIICS to achieve a molar ratio of MIICS to DIISC less than or equal to 10 in the fibrous web at the Yankee dryer, or by indirect treatment of the water in the paper machine so that the ratio of MIICS to DIICS in water would be less than or equal to 50. Molecular sieves can be used to remove specifically some of the MIICS, by donation of monovalent ions to the system, say, at the recirculating white water circuit in a paper machine.

d. Other Means to Selectively Add and/or Remove MIICS and/or DIICS

Not being bound to the theory, it is believed that advances in flocculation and precipitation chemistry can also control the amount of DIICS and/or MIICS in either the solid or liquid phases described herein. It is believed that these processes can accomplish ionic control either by in situ release or removal in the web substrate production process or water streams of MIICS and/or DIICS. Further, it is believed that nanofiltration technology can also control the amount of DIICS and/or MIICS in either of the solid or liquid phases described in this invention. It is believed that a nanofiltration process can accomplish ionic control either by in situ release or removal in the paper production process or water streams of MIICS and/or DIICS.

Not being bound to theory, it is believed that advances in other water desalination processes (like the distillation and reverse osmosis already detailed herein) can be considered as ways to remove MIICS and/or DIICS in water streams. Suitable desalination processes conclude, but not be strictly limited to, vacuum distillation, multi-stage flash distillation, multiple-effect distillation, freeze-thaw, solar evaporation, membrane distillation, and combinations thereof.

Not being bound to theory, it is envisioned that advances in various chelating chemistry processes can be used to remove MIICS and/or DIICS to soften water in fluid streams in the paper machine. These chelating processes can be used in either water or slurry phases and can be based upon non-limiting chelating agents such as citric acid, EDTA, DTPA, sodium phytate/phytic acid, tetrasodium glutamate diacetate, trisodium ethylenediamine disuccinate, and combinations thereof.

Not being bound to theory, we also envision the removal of hardness ions present in water streams by precipitation following the Clark's process. This process provides lime in the form of limewater added to raw water, raising the pH, and shifting the equilibrium of the carbonate species in the water. Dissolved carbon dioxide ($CO_2$) is changed into bicarbonate ($HCO_3^-$) and then carbonate ($CO_3^{-2}$). This action causes calcium carbonate to precipitate due to exceeding the solubility product. Additionally, magnesium can be precipitated as magnesium hydroxide in a double displacement reaction. Both calcium and magnesium ions in the raw water and calcium added in the form of lime are precipitated.

3. Feed Forward Control

The present disclosure also provides for the control of the addition of DIICS accomplished via the utilization of feed forward control whereby the papermaking white water and/or the papermaking pulp streams are monitored to determine the ratio of MIICS to DIICS. If the ratio of MIICS to DIICS is greater than 10, a feed forward control loop could trigger the addition of DIICS (or removal of MIICS as aforementioned) either to the web material immediately before the Yankee dryer, to the creping adhesive make-up system, to the Yankee dryer surface directly, or by any other means envisioned by one skilled in the art, such that the web material that bonds to the Yankee dryer has a ratio MIICS to DIICS of less than or equal to 10. It is believed that the described on-line control process will recognize that all pulps developed for various papermaking processes are different. Therefore, the described on-line control process provides a clear solution to run all pulps at the same reliability on any paper machine.

The control system contemplated utilizes non-destructive ion-selective electrode probes to measure the quantity of mono and divalent ions in a tissue machine stock of any particular unit operation of the papermaking machine having a fluidized phase (i.e., the papermaking fibers are provided in and aqueous environment). For example, the papermaking machine can be provided with a monovalent inorganic ionizable cation species (MIICS) measuring device and a divalent inorganic ionizable cation species (DIICS) measuring device. As the web material is manufactured by the papermaking machine, the molar concentration of the MIICS in can be measured, in discrete time periods or even continuously with the MIICS measuring device. Additionally, the molar concentration of the DIICS can be measured, in discrete time periods or even continuously with the DIICS measuring device. Based upon the data collected by the MIICS measuring device and the DIICS measuring device the molar ratio of the measured molar concentration of the MIICS to the measured molar concentration of the DIICS can be calculated and compared to the desired MIICS to DIICS molar ratio of about less than or equal to 10. If the calculated molar ratio of MIICS to DIICS in the web material is greater than 10 in the web material in any of the stock chest, head box, forming surface, and/or any drying surface, then an amount of DIICS can be added to the papermaking machine.

Similarly, if the data from the papermaking machine water system streams is then coupled with machine throughput data to calculate the addition of divalent ions to reach the desired less than or equal to 50 molar ratio of MIICS to DIICS in these streams. A second control system contemplated utilizes ion selective electrode probes to measure the quantity of MIICS to DIICS in the tissue white water system. This data is then coupled with machine throughput data to calculate the addition of DIICS to reach the desired less than or equal to 50 molar ratio of MIICS to DIICS in the white water. As required, an amount of DIICS can be added to the papermaking machine to obtain the requisite molar ratio of MIICS to DIICS.

Those skilled in the art of papermaking can determine multiple dosing locations throughout the paper machine at all the papermaking machine unit operations to include, but not be limited to, the paper machine white water return loop, the papermaking pulpers, the paper machine stock chests or dilution water streams feeding these chests, the paper machine mix chests, the paper machine head box and it is contemplated the ions being added via spray booms on the wet and/or dry end. Surprisingly, it was discovered that the DIICS aqueous stream is equally effective when coupled with the Yankee creping adhesive spray, Yankee creping adhesive make-up water or via a separate spray boom in conjunction with the Yankee creping adhesive addition.

Additionally, an off-line signal can also be provided to the control system by means of ashing down the papermaking pulp and/or the web material and further measuring the concentration of ionic components (i.e., MIICS and DIICS). By way of non-limiting example, the final pulp product produced by the pulp making process (e.g., the pulp bale, dried product, dried pulp sheets, and/or any intermediate processes) and/or the web material can be ashed by following any of several different standards, namely but not limited to: ISO 1762:2015, ISO/DIS 1762, Tappi T211 om-02, Scan C06, ASTM d586-97, AS/NZ 1301.418, ISO 2144, NBRNM-ISO2144, ABNT NBR 13999:2017, IS 6213 (p.VII):2012, among others. The ashed product can then be measured for MIICS and DIICS molar content by a technique that enables the quantitative analysis of ions such as Atomic Absorption Spectroscopy, Ion Chromatography, Inductively Coupled Plasma with Mass Spectroscopy (ICP-MS), Inductively Coupled Plasma with Optical Emission Spectroscopy (ICP-OES), and the like. Based upon the analysis, an amount of DIICS can be added to the pulp manufacturing process and/or the papermaking machine to obtain the requisite molar ratio of MIICS to DIICS (i.e., a molar ratio of MIICS to DIICS of less than or equal to 10).

4. Feed Back Control

In addition to the previously described feed-forward system, it is envisioned that a feed-back control system can also be utilized to maintain the requisite molar ratio of MIICS to DIICS. Surprisingly it was discovered that the amount of holes present in the web material after the creping process can be readily reduced with the ionic control techniques described herein.

By way of non-limiting example, an on-line sheet defect measuring scanner can be used to detect the amount of holes present in the web material. Alternatively, the control system could utilize ion-selective electrode probes to measure the quantity of mono and divalent ions in a tissue machine stock. For example, the papermaking machine can be provided with a monovalent inorganic ionizable cation species (MIICS) measuring device and a divalent inorganic ionizable cation species (DIICS) measuring device.

As the web material is manufactured by the papermaking machine, the molar concentration of the MIICS and DIICS in can be measured, in discrete time periods or even continuously with the respective MIICS and DIICS measuring devices. Additionally, the molar concentration of the DIICS in can be measured, in discrete time periods or even continuously with the DIICS measuring device.

This data can be coupled with the ion selective electrode probes (described supra) to measure the quantity of MIICS to DIICS in the papermaking white water system. This forms the feed-back control loop of the paper machine. The feed-back control circuitry provided with the paper machine can provide a signal to increase or decrease the molar ratio of MIICS to DIICS by means of increasing or reducing the add-on molar ratio of MIICS or DIICS to meet the required MIICS to DIICS molar ratio of about or less than or equal to 10 in the web material or of about or less than or equal to 50 in the water streams. This signal provided by the feed-back control circuitry can be sent to any of the multiple dosing locations throughout the paper machine at all the papermaking machine unit operations to include, but not be limited to the paper machine white water return loop, papermaking pulpers, paper machine stock chests or dilution water streams feeding these chests, paper machine mix chests, paper machine head box. It is believed that the relevant ionic mixture can be added via spray booms on the wet and/or dry end of the paper machine. Those skilled in the art of papermaking may recognize the use of such a spray boom located on the wet and/or dry end of the paper machine can necessarily provide for a point of easier control and quicker response in order to provide a resulting molar ratio of MIICS to DIICS of about less than or equal to 10 in the solid phase web material evoluting from the paper machine.

An off-line signal can also be provided to the control system by means of ashing down the pulp material and/or web material and further measuring the molar concentration of ionic components (i.e., MIICS and DIICS) therein. By way of non-limiting example, the final pulp product produced by the pulp making process (e.g., the pulp bale, dried product, dried pulp sheets, and/or any intermediate processes) and/or the web material can be ashed by following any of several different standards, namely but not limited to: ISO 1762:2015, ISO/DIS 1762, Tappi T211 om-02, Scan C06, ASTM d586-97, AS/NZ 1301.418, ISO 2144, NBRNM-ISO2144, ABNT NBR 13999:2017, IS 6213 (p.VII):2012, among others. The ashed product can then be measured for MIICS and DIICS molar content by a technique that enables the quantitative analysis of ions such as Atomic Absorption Spectroscopy, Ion Chromatography, Inductively Coupled Plasma with Mass Spectroscopy (ICP-MS), Inductively Coupled Plasma with Optical Emission Spectroscopy (ICP-OES), and the like.

The control system herewith described applies equally to a paper machine or a pulp dryer machine to keep desired or specified amount of ions in the pulp as described in this invention, no matter how the addition or removal of the indicated ions is performed.

Similarly, it is believed that an imaging device can be used to obtain digital images of the web material surface in production to measure the crepe of a moving web material as a basis for feed-back induced corrective actions to implement proper ionic balance as a response to changes in crepe structure. For example, one of skill in the art will recognize that imaging devices can embody methods and apparatii to monitor and control the characteristics of the Yankee dryer creping process by means of optical properties of various points along a creped web material and converting such measurements into defining data. This data can then be fed to the appropriate portion of the papermaking process equipment. It was found that this process can result in a marked increase in quality and efficiency in papermaking.

The present disclosure can also make use of similar imaging devices to provide an input signal to generate an output correction signal to increase or decrease the molar ratio of MIICS to DIICS. This process can be an effective manner to increase or reduce the add-on molar ratio of MIICS or DIICS to meet the required MIICS to DIICS molar ratio of about less than or equal to 10 in the web material or of about less than or equal to 50 in the water streams.

It should be understood that the output correction signal created by this described feed-back system can be sent to any of the multiple dosing locations throughout the paper machine at all the papermaking machine unit operations to include, but not be limited to, the paper machine white water return loop, papermaking pulpers, paper machine stock chests or dilution water streams feeding these chests, paper machine mix chests, paper machine head box. Further, it is contemplated the MIICS and/or DIICS being added to the particular dosing location can be provided via spray booms on the wet and/or dry end of the papermaking machine.

In yet another non-limiting embodiment, an imaging device used to obtain digital images of the web material surface can be used to collect topographic three-dimensional information of the web material sheet that can be used to control softness of the resulting tissue and/or towel sheet. This topographic three-dimensional information of the web material sheet can be used as a basis for corrective actions to implement as response to changes in web material structure.

It is also believed in another non-limiting embodiment that an imaging device used to obtain digital images of the web material surface can be used to collect topographic three-dimensional information of the web material can be used as an input signal to generate an output correction signal. This output correction signal can then be used by control circuitry known by those of skill in the art to increase or decrease the molar ratio of MIICS to DIICS by increasing or reducing the add-on molar ratio of MIICS to DIICS to meet the required molar ratio of about less than or equal to 10 in the web material or of about less than or equal to 50 in the relevant papermaking water streams. It should be understood that the output correction signal created by this described feed-back system can be sent to any of the multiple dosing locations throughout the paper machine at all the papermaking machine unit operations to include, but not be limited to, the paper machine white water return loop, papermaking pulpers, paper machine stock chests or dilution water streams feeding these chests, paper machine mix chests, paper machine head box. Further, it is contemplated the MICCS and/or DIICS being added to the particular dosing location can be provided via spray booms on the wet and/or dry end of the papermaking machine.

Any dimensions and/or values disclosed herein are not to be understood as being strictly limited to the exact numerical values recited. Instead, unless otherwise specified, each such dimension and/or value is intended to mean both the recited dimension and/or value and a functionally equivalent range surrounding that dimension and/or value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for manufacturing a creped web material on a papermaking machine having a Yankee drum drying system, wherein said process comprises the steps of:
    a) producing said web material with said papermaking machine;
    b) measuring a molar amount of a monovalent inorganic ionizable cation species (MIICS) in said web material;
    c) measuring a molar amount of a divalent inorganic ionizable cation species (DIICS) in said web material;
    d) calculating a molar ratio of said measured molar amount of said MIICS to said measured molar amount of said DIICS in said web material;
    e) determining if said molar ratio of MIICS to DIICS is about less than or equal to 10; and,
    f) if said molar ratio of MIICS to DIICS is greater than about 10, adding an amount of DIICS to said papermaking machine to adjust said molar ratio of MIICS to DIICS so said web material adhering to said Yankee drum drying system has a molar ratio of MIICS to DIICS of about less than or equal to 10.

2. The process of claim 1 wherein said step d) further comprises the step of adding an amount of DIICS to said papermaking machine to adjust said molar ratio of MIICS to DIICS so said web material adhering to said Yankee drum drying system has a molar ratio of MIICS to DIICS ranging from about 0.1 to about 10.

3. The process of claim 2 wherein said step d) further comprises the step of adding an amount of DIICS to said papermaking machine to adjust said molar ratio of MIICS to DIICS so said web material adhering to said Yankee drum drying system has a molar ratio of MIICS to DIICS ranging from about 2 to about 7.

4. The process of claim 2 wherein said step d) further comprises the step of adding an amount of DIICS to said papermaking machine to adjust said molar ratio of MIICS to DIICS so said web material adhering to said Yankee drum drying system has a molar ratio of MIICS to DIICS ranging from about 4 to about 6.

5. The process of claim 1 wherein said MIICS is selected from the group consisting of $Li^+$, $Na^+$, $K^+$, $Rb^+$, counter ions, source salts, oxides, derivatives, and combinations thereof and said DIICS is selected from the group consisting of $Be^{+2}$, $Mg^{+2}$, $Ca^{+2}$, $Sr^{+2}$, $Ba^{+2}$, $Ra^{+2}$, counter ions, source salts, oxides, derivatives, and combinations thereof.

6. The process of claim 5 wherein said MIICS is $Na^+$ and said DIICS is $Ca^{+2}$.

7. The process of claim 1 wherein said process further comprises the step of, prior to step a), supplying said papermaking machine with one or more fibers.

8. The process of claim 7 further comprising the step of modifying said one or more fiber before delivery to said papermaking machine by the addition of DIICS at a level that provides the molar ratio of has a molar ratio as measured in the solid phase of MIICS to DIICS of about less than or equal to 10.

9. The process of claim 8 wherein said process further comprises the step of manufacturing said one or more fibers with a pulp making process, said pulp making process having a process selected from the group consisting of a pulping process, a bleaching process, and a drying process.

10. The process of claim 9 wherein said process further comprises the step of adding said DIICS to at least one of said pulping process, said bleaching process, or said drying process at a level that provides the molar ratio of has a molar ratio as measured in the solid phase of MIICS to DIICS of about less than or equal to 10.

11. The process of claim 1 wherein said process further comprises the step of, prior to step a), providing said papermaking machine with a wet structure formation section, and said step d) further comprises the step of adding said amount of DIICS to said wet structure formation section.

12. The process of claim 1 wherein said process further comprises the step of, prior to step a), providing said papermaking machine with a headbox wet ingredient mixing system and said step d) further comprises the step of adding said amount of DIICS to said headbox wet ingredient mixing system.

13. A process for manufacturing a creped web material on a papermaking machine having a Yankee drum drying system, wherein said process comprises the steps of:
 a) producing said web material with said papermaking machine;
 b) measuring a molar amount of a monovalent inorganic ionizable cation species (MIICS) in said web material;
 c) measuring a molar amount of a divalent inorganic ionizable cation species (DIICS) in said web material;
 d) calculating a molar ratio of said measured molar amount of said MIICS to said measured molar amount of said DIICS in said web material;
 e) determining if said molar ratio of MIICS to DIICS is about less than or equal to 10; and,
 f) if said molar ratio of MIICS to DIICS is greater than about 10, applying an amount of DIICS to a surface of said Yankee drum drying system to adjust said molar ratio of MIICS to DIICS so said web material adhering to said Yankee drum drying system has a molar ratio of MIICS to DIICS of about less than or equal to 10.

14. The process of claim 13 wherein said MIICS is selected from the group consisting of $Li^+$, $Na^+$, $K^+$, $Rb^+$, counter ions, source salts, oxides, derivatives, and combinations thereof and said DIICS is selected from the group consisting of $Be^{+2}$, $Mg^{+2}$, $Ca^{+2}$, $Sr^{+2}$, $Ba^{+2}$, $Ra^{+2}$, counter ions, source salts, oxides, derivatives, and combinations thereof.

15. The process of claim 14 wherein said MIICS is $Na^+$ and said DIICS is $Ca^{+2}$.

16. The process of claim 14 wherein said MIICS is $Na^+$ and said DIICS is $Ca^{+2}$.

17. The process of claim 13 wherein said MIICS is selected from the group consisting of $Li^+$, $Na^+$, $K^+$, $Rb^+$, counter ions, source salts, oxides, derivatives, and combinations thereof and said DIICS is selected from the group consisting of $Be^{+2}$, $Mg^{+2}$, $Ca^{+2}$, $Sr^{+2}$, $Ba^{+2}$, $Ra^{+2}$, counter ions, source salts, oxides, derivatives, and combinations thereof.

18. A process for manufacturing a creped web material on a papermaking machine having a Yankee drum drying system, wherein said process comprises the steps of:
 a) providing said papermaking machine with a white water loop section, said white water loop section providing said papermaking machine with an aqueous stream;
 b) producing said web material with said papermaking machine;
 c) measuring a molar amount of a monovalent inorganic ionizable cation species (MIICS) in said web material;
 d) measuring a molar amount of a divalent inorganic ionizable cation species (DIICS) in said web material;
 e) calculating a molar ratio of said measured molar amount of said MIICS to said measured molar amount of said DIICS in said web material;
 f) determining if said molar ratio of MIICS to DIICS is about less than or equal to 10; and,
 g) if said molar ratio of MIICS to DIICS is greater than about 10, adding an amount of DIICS to said white water loop section of said papermaking machine to adjust said molar ratio of MIICS to DIICS in said aqueous stream to about less than or equal to 50.

19. The process of claim 18 wherein said MIICS is selected from the group consisting of $Li^+$, $Na^+$, $K^+$, $Rb^+$, counter ions, source salts, oxides, derivatives, and combinations thereof and said DIICS is selected from the group consisting of $Be^{+2}$, $Mg^{+2}$, $Ca^{+2}$, $Sr^{+2}$, $Ba^{+2}$, $Ra^{+2}$, counter ions, source salts, oxides, derivatives, and combinations thereof.

20. The process of claim 19 wherein said MIICS is $Na^+$ and said DIICS is $Ca^{+2}$.

21. A process for manufacturing a creped web material on a papermaking machine having a Yankee drum drying system, wherein said process comprises the steps of:
 a) providing said papermaking machine with a fresh water makeup system, said fresh water makeup system providing said papermaking machine with an aqueous stream;
 b) producing said web material with said papermaking machine;
 c) measuring a molar amount of a monovalent inorganic ionizable cation species (MIICS) in said web material;
 d) measuring a molar amount of a divalent inorganic ionizable cation species (DIICS) in said web material;
 e) calculating a molar ratio of said measured molar amount of said MIICS to said measured molar amount of said DIICS in said web material;
 f) determining if said molar ratio of MIICS to DIICS in said web material is about less than or equal to 10; and,
 g) if said molar ratio of MIICS to DIICS is greater than about 10, adding an amount of DIICS to said fresh water makeup system of said papermaking machine to adjust a molar ratio of MIICS to DIICS in said aqueous stream to less than or equal to 50.

22. The process of claim 21 wherein said MIICS is selected from the group consisting of $Li^+$, $Na^+$, $K^+$, $Rb^+$, counter ions, source salts, oxides, derivatives, and combinations thereof and said DIICS is selected from the group consisting of $Be^{+2}$, $Mg^{+2}$, $Ca^{+2}$, $Sr^{+2}$, $Ba^{+2}$, $Ra^{+2}$, counter ions, source salts, oxides, derivatives, and combinations thereof.

23. The process of claim 22 wherein said MIICS is $Na^+$ and said DIICS is Ca'.

24. A process for manufacturing a creped web material on a papermaking machine having a Yankee drum drying system, wherein said process comprises the steps of:
 a) supplying said Yankee drum drying system with a creping adhesive;
 b) applying said creping adhesive to a surface of said Yankee drum drying system;
 c) producing said web material with said papermaking machine;
 d) measuring a molar amount of a monovalent inorganic ionizable cation species (MIICS) in said web material;

e) measuring a molar amount of a divalent inorganic ionizable cation species (DIICS) in said web material;

f) calculating a molar ratio of said measured molar amount of said MIICS to said measured molar amount of said DIICS in said web material;

g) determining if said molar ratio of MIICS to DIICS is about less than or equal to 10; and, h) if said molar ratio of MIICS to DIICS is greater than about 10, adding an amount of DIICS to said creping adhesive so that said web material upon contact with said creping adhesive disposed upon said surface of said Yankee drum drying system DIICS has a molar ratio of MIICS to DIICS of about less than or equal to 10.

25. The process of claim 24 wherein said MIICS is selected from the group consisting of $Li^+$, $Na^+$, $K^+$, $Rb^+$, counter ions, source salts, oxides, derivatives, and combinations thereof and said DIICS is selected from the group consisting of $Be^{+2}$, $Mg^{+2}$, $Ca^{+2}$, $Sr^{+2}$, $Ba^{+2}$, $Ra^{+2}$, counter ions, source salts, oxides, derivatives, and combinations thereof.

26. The process of claim 25 wherein said MIICS is $Na^+$ and said DIICS is $Ca^{+2}$.

27. The process of claim 24 further comprising the step of providing said creping adhesive with at least one compound selected from the group consisting of adhesive compounds, creping aids, release aids, creping adhesive glass transition point modifying compounds, and combinations thereof.

28. The process of claim 24 wherein said step of adding an amount of DIICS to said creping adhesive further comprises the step of adding an amount of DIICS to said creping adhesive prior to said creping adhesive being applied to a surface of said Yankee drum drying system.

29. The process of claim 24 wherein said step of adding an amount of DIICS to said creping adhesive further comprises the step of adding an amount of DIICS to said creping adhesive after said creping adhesive has been applied to a surface of said Yankee drum drying system.

30. The process of claim 29 wherein said step of adding an amount of DIICS to said creping adhesive after said creping adhesive has been applied to a surface of said Yankee drum drying system further comprises the step of continuously applying said DIICS to said creping adhesive.

31. The process of claim 24 wherein said step of adding an amount of DIICS to said creping adhesive further comprises the step of applying said amount of DIICS to said surface of said Yankee drum drying system prior to said creping adhesive being applied to said surface of said Yankee drum drying system.

32. The process of claim 31 wherein said step of applying said amount of DIICS to said surface of said Yankee drum drying system prior to said creping adhesive being applied to said surface of said Yankee drum drying system further comprises the step of continuously applying said DIICS to said surface of said Yankee drum drying system.

33. The process of claim 24 wherein said step of step of adding an amount of DIICS to said creping adhesive further comprises the step of adding an amount of DIICS to said creping adhesive to modify the glass transition temperature of said creping adhesive.

34. A process for manufacturing a creped web material on a papermaking machine having a Yankee drum drying system, wherein said process comprises the steps of:

a) producing said web material with said papermaking machine;

b) measuring a molar amount of a monovalent inorganic ionizable cation species (MIICS) in said web material;

a) measuring a molar amount of a divalent inorganic ionizable cation species (DIICS) in said web material;

b) calculating a molar ratio of said measured molar amount of said MIICS to said measured molar amount of said DIICS in said web material;

e) determining if said molar ratio of MIICS to DIICS is about less than or equal to 10; and, f) if said molar ratio of MIICS to DIICS is greater than about 10, applying an amount of DIICS to said web material after said web material has been adhered to a surface of said Yankee drum drying system to adjust said molar ratio of MIICS to DIICS so said web material adhered to said Yankee drum drying system has a molar ratio of MIICS to DIICS of about less than or equal to 10.

* * * * *